United States Patent [19]
Takahashi et al.

[11] Patent Number: 6,140,360
[45] Date of Patent: *Oct. 31, 2000

[54] ANTIFUNGAL AGENT

[75] Inventors: Akira Takahashi; Jun-ichi Masuda; Ken-ichi Tanaka; Muneaki Kanou; Sanae Tanaka; Toshiaki Segawa; Shigeo Nozoe, all of Ibaraki, Japan

[73] Assignee: TOA Gosei Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/242,225

[22] PCT Filed: Jun. 6, 1997

[86] PCT No.: PCT/JP97/01929

§ 371 Date: Jul. 28, 1999

§ 102(e) Date: Jul. 28, 1999

[87] PCT Pub. No.: WO98/06388

PCT Pub. Date: Feb. 19, 1998

[30] Foreign Application Priority Data

Aug. 13, 1996 [JP] Japan .................................. 8-231297

[51] Int. Cl.[7] ...................... A61K 31/34; A61K 31/215; A61K 31/19

[52] U.S. Cl. .......................... 514/461; 514/429; 514/546; 514/547; 514/557; 514/574

[58] Field of Search .................... 514/461, 529, 514/546, 547, 557, 574

[56] References Cited

U.S. PATENT DOCUMENTS 5,840,927 12/1998 Nozoe et al. ........................ 549/458

FOREIGN PATENT DOCUMENTS

96/25385A1 8/1996 WIPO .

OTHER PUBLICATIONS

Asakawa et al., "Cyptoporic Acids A–G, Drimane–Type Sesquiterpenoid Ethers of Isocitric Acid from the Fungus Cryptoporus Volvatus", Phytochem., vol. 31 No. 2, pp. 579–592, 1992.

*Primary Examiner*—Rebecca Cook
*Attorney, Agent, or Firm*—Fish & Richardson P.C.

[57] ABSTRACT

A cryptoporic acid derivative as a sesquiterpene compound having a drimane skeleton has been isolated from the fruiting body extract of a Basidiomycetes and found to have an antifungal effect.

3 Claims, 17 Drawing Sheets

ANTIFUNGAL AGENT

This is a 371 of PCT/JP97/01929 filed Jun. 6, 1997

TECHNICAL FIELD

This invention relates to an antifungal agent comprising as an active ingredient a derivative of cryptoporic acid isolated from a fruiting body of Basidiomycetes. The compound is useful as an antibacterial or antifungal agent or a starting material for manufacturing these agents. The present invention thus pertains to the field of pharmaceuticals or their production.

BACKGROUND ART

Antimicrobial drugs, and especially antibiotics, have developed remarkably. In contrast, antifungal drugs are lacking in variety and effectiveness. In particular, the opportunistic mycoses of internal organs caused by infections with Candida, Aspergillus, and Cryptococcus due to a decreased bodily defense capability resulting from extensive administration of carcinostatic agents, immunosuppressants, steroid hormones, and acquired immunodeficiency syndrome (AIDS) in recent years are posing significant medical problems. Therefore, there is a strong demand for developing drugs for mycoses.

Biologically active agents contained in mushrooms have been examined in various ways since early times. *Ganoderma applanatum*, and *Coriolus versicolor* have been conventionally used as oriental drugs and folk remedies effective for stomach, esophageal, mammary, and prostate cancers. In particular, β-D-glucan-protein complex (PS-K) extracted from cultured mycelium from *Corliolus versicolor* has been used widely as an anticancer medicament. It was reported in Korea that Lee et al. (1981) and Kim et al. (1982) obtained from *Cryptoporus volvatus* a protein-polysaccharide with anticancer activity from water extract and ergosterol from chloroform-methanol extract (Asakawa et al., Trans. Mycol. Soc. Japan 29: 281–296, 1998). Asakawa et al. reported obtaining various derivatives of cryptoporic acid as bitter elements from the *Cryptoporus volvatus* and that Cryptoporic acid different from those mentioned above has been obtained from culture extracts (M. Hirotani et al., Phytochemistry 30(5), 1555–1559 (1991)). It has also been reported that cryptoporic acid derivatives can be obtained from cultured *Ganoderma neojaponicum*. Furthermore, other cryptoporic acid derivatives and compounds analogous to cryptoporic acid derivatives are reported to have been obtained from *Haploporus odorus* (Y. Morita et al., Biosci. Biotech. Biochem. 59(19): 2008–2009 (1995)).

Biological activities of cryptoporic acid reportedly include active oxygen inhibitory activity (Asakawa et al., Trans. Mycol. Soc. Japan 29: 281–296, 1988), inhibition of germination of rice (T. Hashimoto et al., Tetrahydron Lett. 28(50): 6303–6304 (1987)), and an inhibitory effect on chemical carcinogenesis (T. Narisawa et al., Jpn. J. Cancer Res. 83: 830–834 (1992)).

Cryptoporic acid derivatives described above with partially known properties form a group of compounds described by formula 4.

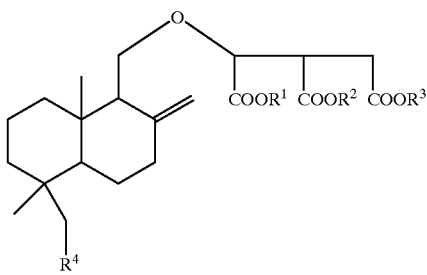

(4)

wherein $R^4$ represents a hydrogen atom or a hydroxyl group, and $R^1$, $R^2$, and $R^3$ may be the same or different from each other and each represents a hydrogen atom, an alkyl group (particularly a lower alkyl group, more specifically a methyl group), and an alkali metal such as sodium or potassium.

DISCLOSURE OF THE INVENTION

An objective of the present invention is to provide compounds useful as an antibacterial or antifungal agent or as a starting material for manufacturing these agents, and an antifungal agent.

The present inventors isolated sesquiterpene compounds, more specifically various cryptoporic acid derivatives consisting of sesquiterpene with the drimane skeleton and isocitric acid, from extracts of a fruiting body of *Cryptoporus volvatus*, a mushroom of the Polyporaceae family, and found that the cryptoporic acid derivatives possessed antifungal activity. The present inventors further sought novel biologically active components contained in mushrooms. They also studied ardently to find compounds which had strong antifungal activities on the fungi mentioned above that cause opportunistic visceral mycosis and which could be used as effective antifungal agents. As a result, the present inventors succeeded in isolating various cryptoporic acid derivatives, including novel compounds, from extracts obtained from a fruiting body of *Roseofomes subflexibilis* (Berk. et Curt.) Aoshi, a mushroom of the Polyporaceae family, with lower alcohol, ethyl acetate, or acetone. These compounds could be useful as starting materials for manufacturing compounds with antifungal activities as well as antifungal agents themselves. Thus, the present invention has been completed.

The present invention relates to an antifungal agent comprising as an active ingredient a cryptoporic acid derivative with a hydroxyl group represented by formula 1 or a dimer thereof:

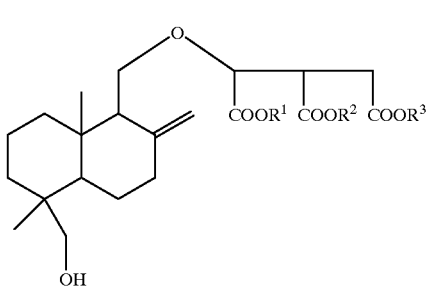

(1)

wherein $R^1$, $R^2$, and $R^3$ may be the same or different from each other and each represents a hydrogen atom, an alkyl group, or an alkali metal, and —$COOR^2$ and —$COOR^3$ may form together a five-membered lactone ring.

A cryptoporic acid with a five-membered lactone ring is shown by formula 2:

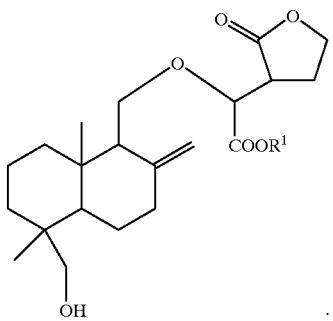

(2)

Dimer means a compound in which two cryptoporic acid derivatives combine through an ester bond between a hydroxyl group of one derivative and a carboxyl group of the other derivative. It sometimes forms a ring structure through two ester bonds. The alkyl group may be a lower alkyl, especially a methyl group. The alkali metals include sodium and potassium.

The cryptoporic acid derivatives of the present invention represented by formula 1 can be obtained by extracting a fruiting body of *Cryptoporus volvatus*, a mushroom of Polyporaceae family, grown on a dead "akamatsu" (a Japanese red pine), with a solvent. More specifically, fruiting bodies of *Cryptoporus volvatus* are cut into pieces and immersed in a solvent such as ethyl acetate at room temperature for one to three days to extract active ingredients. The thus-obtained extracts are purified by a combination of usual means for isolating compounds such as silica gel column chromatography, preparatory thin-layer chromatography, and high-performance liquid chromatography, to separate the desired compounds.

The cryptoporic acid derivatives with a five-membered lactone ring of the present invention represented by formula 2 can be obtained from *Roseofomes subflexibilis*, a mushroom of the Polyporaceae family. *Roseofomes subflexibilis* grows plentifully from summer to autumn, mainly on fallen trees of *Quercus acutissina* or the like in woods. The compounds can be extracted from the fruiting body. More specifically, fruiting bodies of *Roseofomes subflexibilis* are cut into pieces and immersed in acetone, ethyl acetate, or lower alcohol such as methanol, at room temperature for one to three days. After the thus-obtained extract is concentrated under reduced pressure, the resulting syrupy residue is suspended in water and extracted with ethyl acetate or a similar solvent. The extract thus obtained is purified by a combination of usual methods for separating antibiotics such as silica gel column chromatography, preparatory thin-layer chromatography, and high-performance liquid chromatography to obtain novel compounds represented by formula 3 as colorless columnar crystals. Methyl groups of the thus-obtained compounds can be converted to hydrogen atoms or lower alkyl groups such as ethyl or propyl by commonly used methods such as transesterification.

An antifungal agent containing a cryptoporic acid derivative of the present invention as described above as an active ingredient is useful as a therapeutic agent for mycoses caused by mycetes such as fungi or yeasts in various animals including humans. It can be used as tablets, capsules, etc. for oral administration, and as solutions, suspensions, and ointments for parenteral administration. Though the dose may vary depending on the disease severity, body weight of patients, etc., it may generally range from about 10 to 500 mg once or several times a day. Injections may be conducted by adding the compound to installation fluids. The required unit dose of the compound can be formulated into dosage forms together with commonly used vehicles, carriers, extenders, excipients, binders, lubricants, buffers, antioxidants, antiseptics, stabilizers, and flavors.

BEST MODE FOR IMPLEMENTING THE INVENTION

The present invention will be explained below in more detail with reference to examples, but is not to be construed to be limited thereto.

EXAMPLE 1

Preparation of Cryptoporic Acid Derivatives

1. Fruiting bodies of *Cryptoporus volvatus* (about 27 g) collected at Omaeyama in Ibaragi prefecture in May 1996 were extracted with ethyl acetate at room temperature for one day. The same procedure was repeated to obtain 3.57 g of ethyl acetate extract. The ethyl acetate extract was subjected to silica gel column chromatography using a mixed solvent consisting of chloroform and ethyl acetate and a mixed solvent consisting of chloroform and methanol. The cryptoporic acid derivative-containing fractions thus obtained were subjected to silica gel column chromatography using a chloroform-methanol mixed solvent. Some compounds were crystallized. The following three cryptoporic acid derivatives were obtained (hereinafter referred to as cryptoporic acid A (formula 5), cryptoporic acid B (formula 6), and cryptoporic acid D (formula 7) according to the conventional definition).

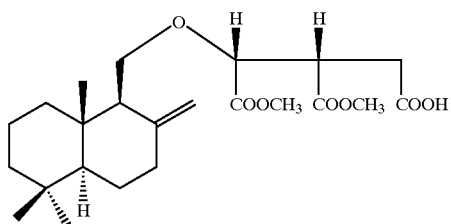

(5)

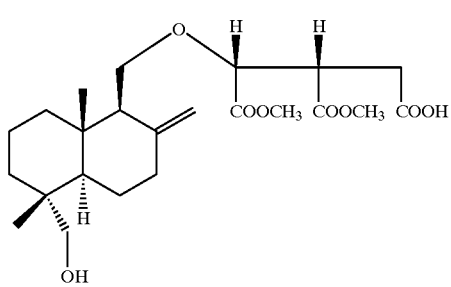

(6)

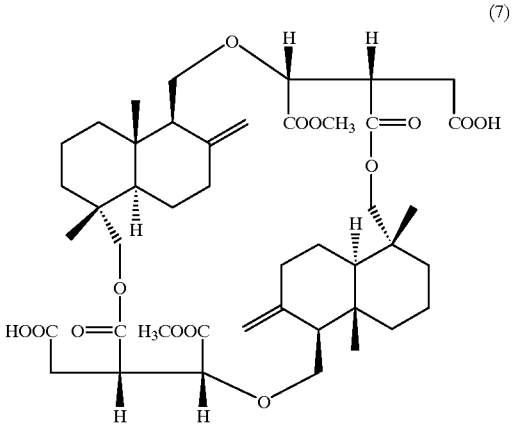

(7)

These structures were determined by conducting TLC, $^1$H-NMR, $^{13}$C-NMR, and mass spectrometry and comparing the data with those described in the literature of Asakawa et al. (Trans. Mycol. Soc. Japan 29: 281–296 (1988) and Phytochemistry 31(2): 579–592 (1992)).

Figure 1:
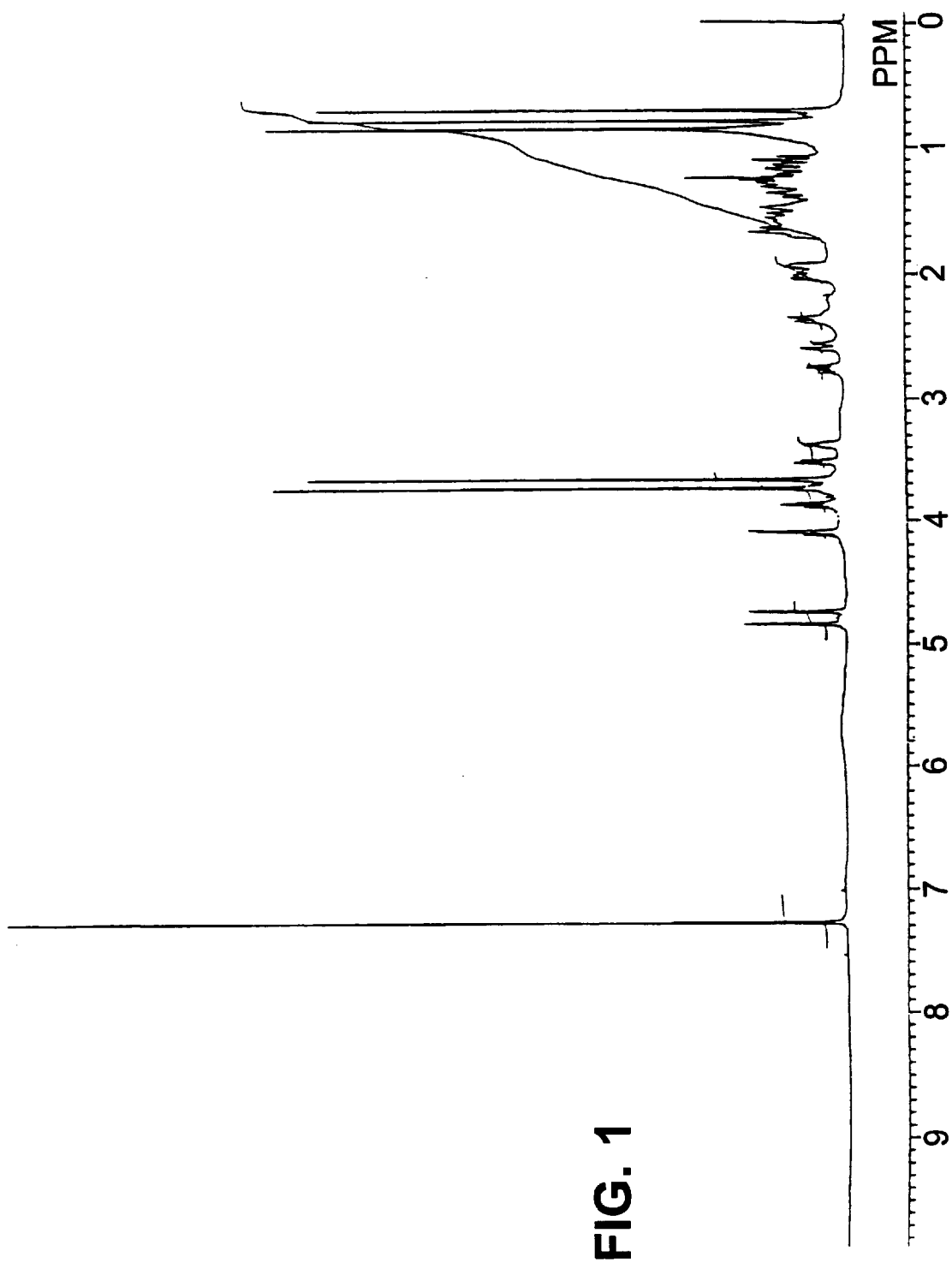
FIG. 1 shows a $^1$H-NMR chart of cryptoporic acid A.
Figure 2:
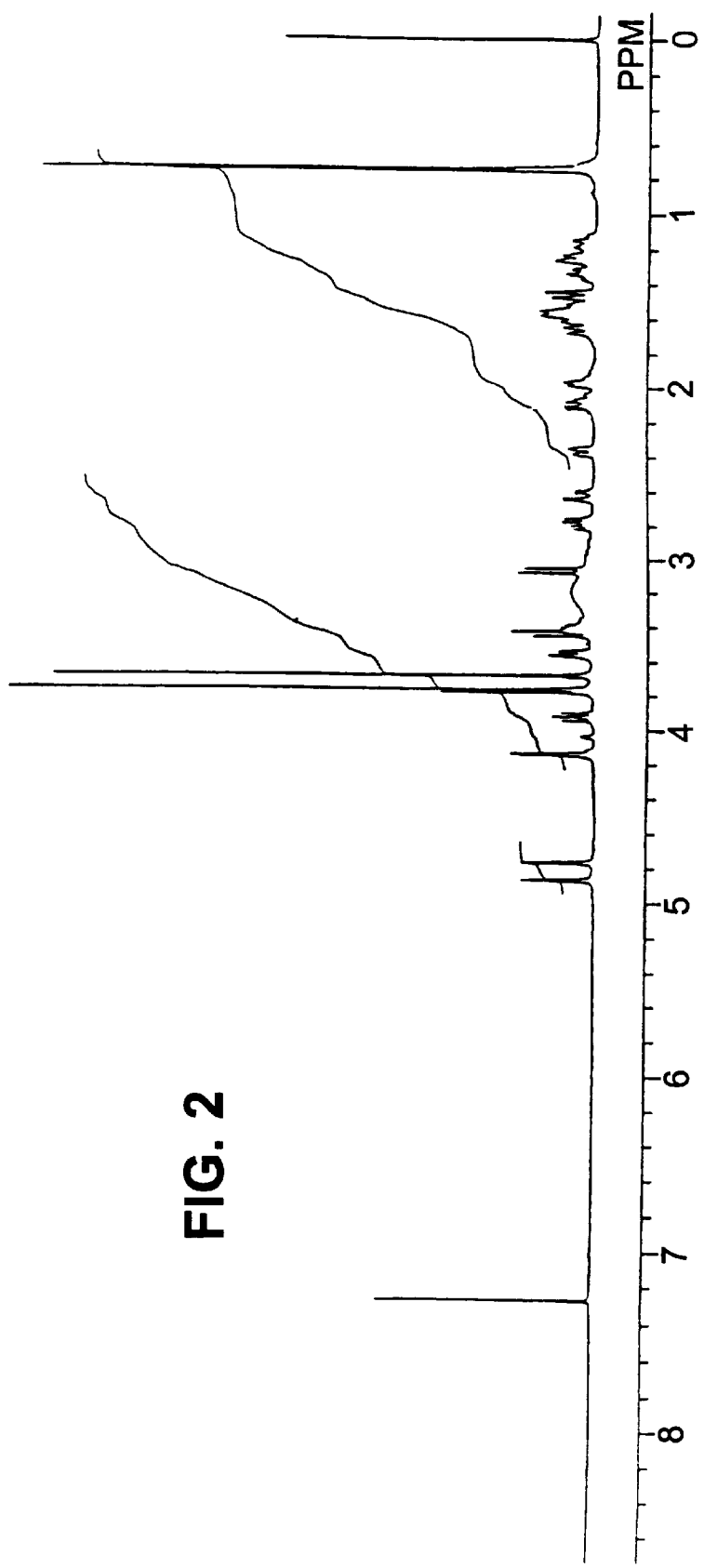
FIG. 2 shows a $^1$H-NMR chart of cryptoporic acid B.
Figure 3:
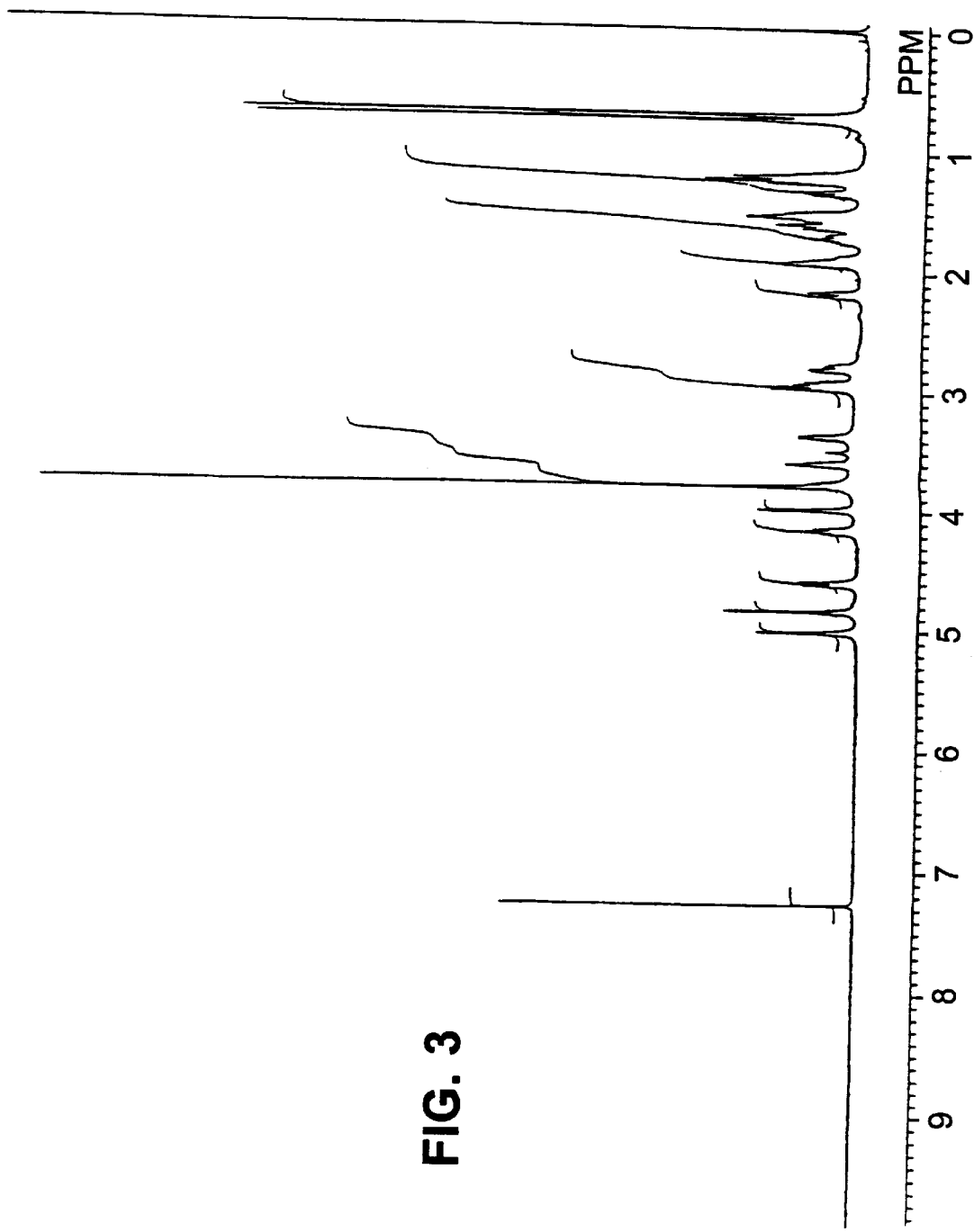
FIG. 3 shows a $^1$H-NMR chart of cryptoporic acid D.

The resulting compounds were identified as cryptoporic acids A, B, and D. Yields of these compounds were 40.2 mg for cryptoporic acid A, 21.9 mg for cryptoporic acid B, and 63.2 mg for cryptoporic acid D. $^1$H-NMR charts of these compounds are shown in FIGS. 1 to 3.

2. A novel sesquiterpene compound (WO96/25385) was obtained by extracting fruitingbodies of Roseofomes sub-flexibilis (Berk. et Curt. z) Aoshi, a mushroom of the Polyporaceae family, with lower alcohol. The resulting extract was hydrolyzed to synthesize a cryptoporic acid derivative (hereinafter referred to as cryptoporic acid H (formula 8) according to the conventional definition).

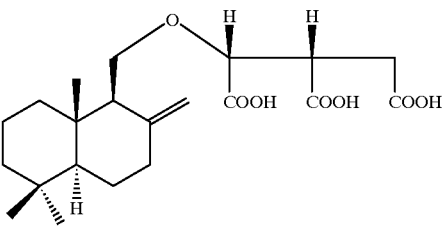

(8)

More specifically, fruiting bodies of Roseofomes subflexibilis (60 g) collected at Aobayama in Sendai-shi in October 1992 were immersed in 300 ml of acetone for one day to obtain acetone extract. The residue was immersed in 300 ml of methanol to obtain methanol extract. After removing the solvent from the respective extracts under reduced pressure, water (25 ml) was added to each residue, and the solution was partitioned with ethyl acetate (50 ml×2). The respective ethyl acetate layers were confirmed to contain the novel compound by thin-layer chromatography. These layers were then combined.

The ethyl acetate fraction (1.52 g) was subjected to silica gel column chromatography (16 g; 1.5 cm ID×20 cm) and eluted with an n-hexane/ethyl acetate mixed solvent, a chloroform/ethyl acetate mixed solvent, and a chloroform/methanol mixed solvent.

Fractions eluted with chloroform/methanol=95/5 to 90/10 were combined and concentrated under reduced pressure. The resulting residue (308 mg) was subjected to silica gel column chromatography (eluent, chloroform/methanol=99/1 to 90/10) and 149 mg of fractions eluted with chloroform/methanol=98/2 to 96/4 were collected.

In the same manner, 68 mg of fractions eluted with chloroform/methanol=95/5 to 90/10 were obtained from fractions eluted with chloroform/methanol=90/10 to 80/20 (161 mg).

The fractions thus obtained were purified by preparatory thin-layer chromatography (TLC plate, silica gel 60 $F_{254}$, 20 cm×20 cm×0.5 mm (Merck); developing solvent, chloroform/methanol=95/5 and 90/10) to obtain a novel colorless, syrupy substance.

The novel compound was named TG 103, and its yield was 31.1 mg.

The structural formula and physicochemical properties of the novel compound are shown below.

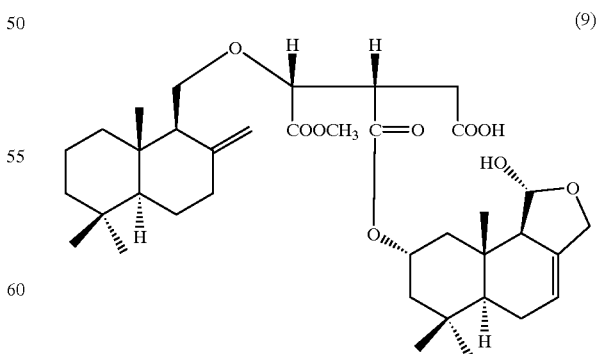

(9)

Figure 4:
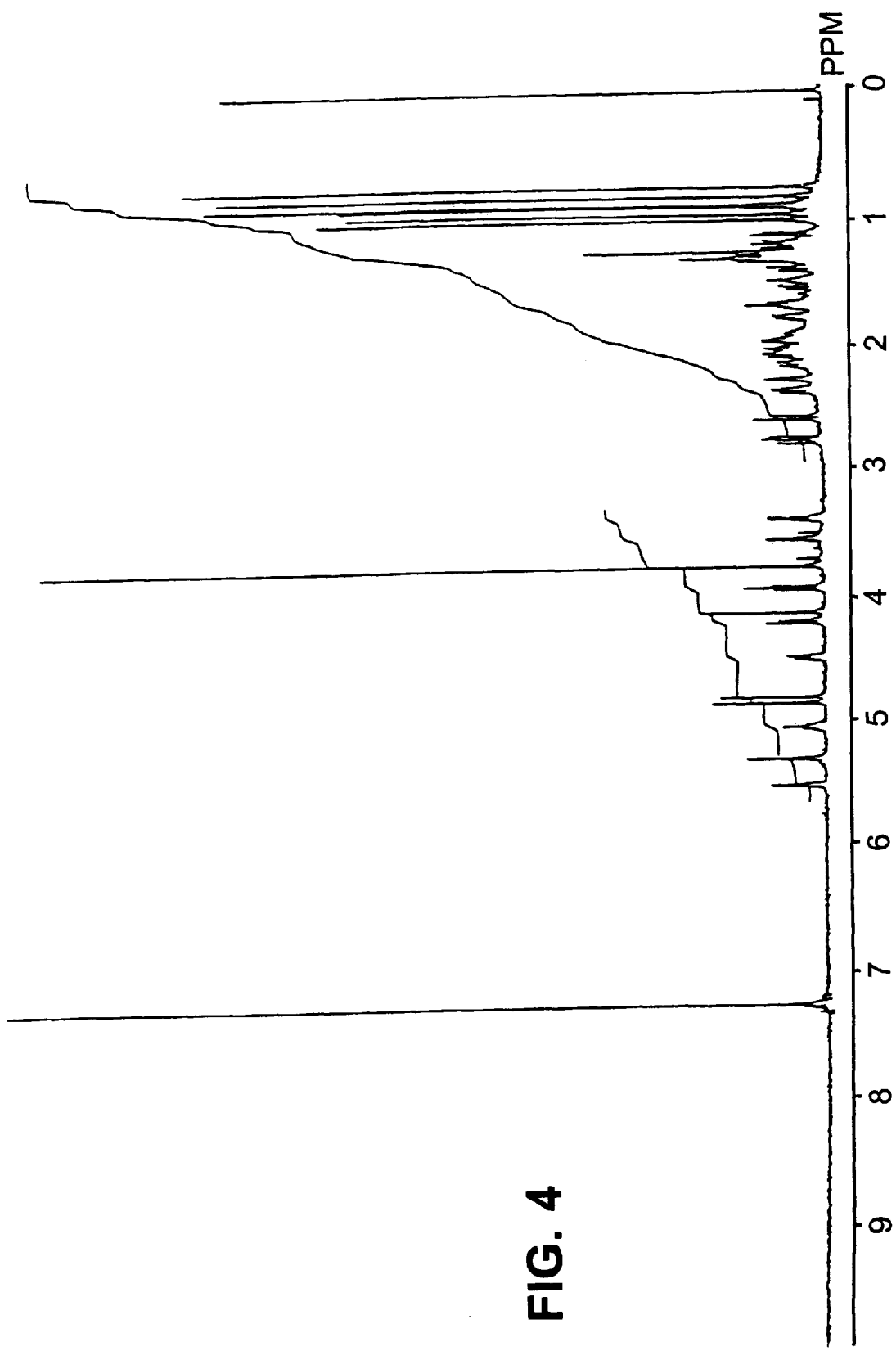
FIG. 4 shows the $^1$H-NMR spectrum of TG-103.
Figure 5:
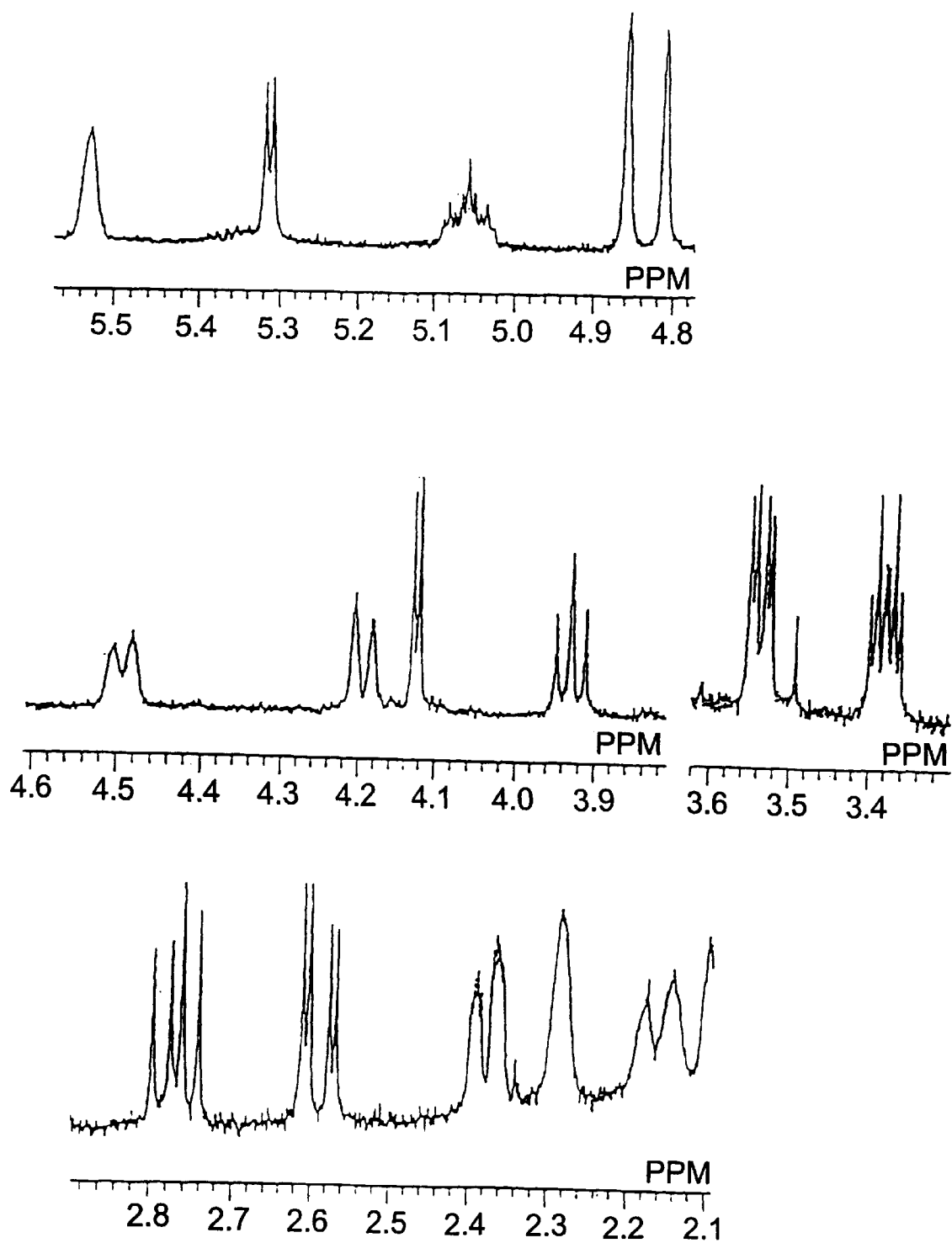
FIG. 5 shows a magnification of a part of the $^1$H-NMR spectrum of TG-103.
Figure 6:
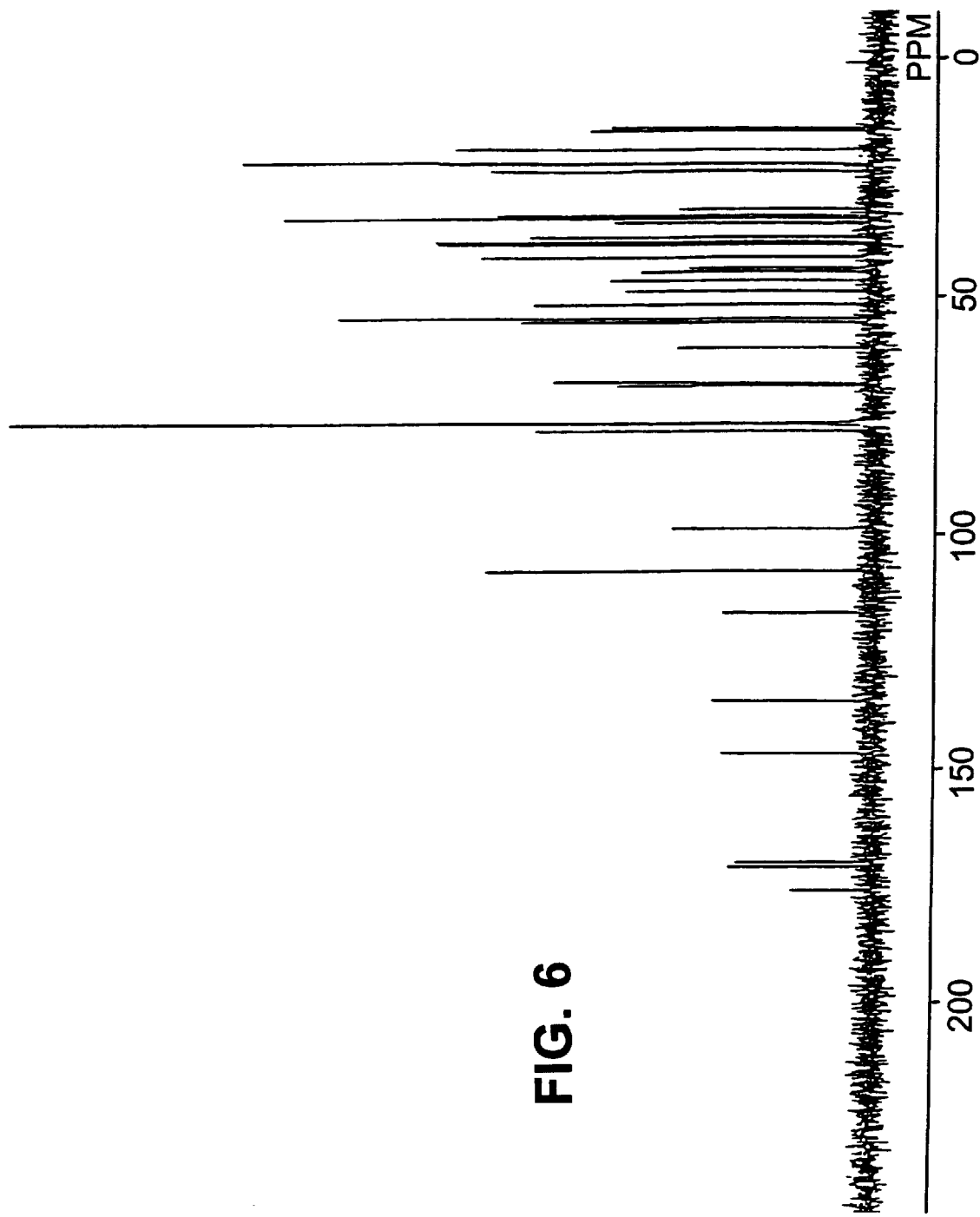
FIG. 6 shows the $^{13}$C-NMR spectrum of TG-103.

Physicochemical Properties of TG 103
 (1) Appearance: Colorless, syrupy
 (2) Specific rotation: $[\alpha]_D^{26}$ +10.6° (c=0.17, chloroform)
 (3) Molecular weight: 644
 (4) Molecular formula: $C_{37}H_{56}O_9$
 (5) FAB mass spectrum: m/z 667 [(M+Na)$^+$]
 (6) HREI mass spectrum: m/z 626.3838 (M$^+$-H$_2$O:$C_{37}H_{54}O_8$) Found: 626.3819
 (7) Infrared absorption spectrum (cm$^{-1}$) υmax (CHCl$_3$): 3625–2400 (br), 2940, 2860, 1750 (sh), 1730, 1640, 1460, 1440, 1390, 1360, 1320–1140 (br), 1130, 1010
 (8) $^1$H-NMR spectrum: As shown in FIGS. 4 and 5
 (9) $^{13}$C-NMR spectrum: As shown in FIG. 6
 (10) Solubility:
  Easily soluble in methanol, acetone, and ethyl acetate; soluble in chloroform; and slightly soluble in water
 (11) Rf value: Silica gel thin-layer chromatography with Kieselgel
  60F$_{254}$ (Merck)
  0.29 (chloroform/methanol=90/10)
  0.07 (chloroform/ethyl acetate/methanol=15/5/1)
 (12) Color reaction: Ehrlich reagent-positive (purple red)

One ml of a 1 N sodium hydroxide aqueous solution was added to an ethanol solution of TG 103 (32 mg), and the solution was refluxed for 3 hours. After the reaction was completed, the reaction solution was diluted with 4 ml of water and washed twice with 10 ml of ethyl acetate. The aqueous phase was made acidic with 1N hydrochloric acid and extracted twice with 10 ml of ethyl acetate. The resulting extract was washed with water then with saturated brine. After the ethyl acetate phase was dried over magnesium sulfate, the solvent was removed by distillation. The residue was purified by ODS column chromatography (COSMOSIL 75C18 OPN, 2.0 cm ID×17.5 cm; eluent, water-methanol= 30/70 to 0/100) to obtain 13 mg of cryptoporic acid H as white powder.

Figure 7:
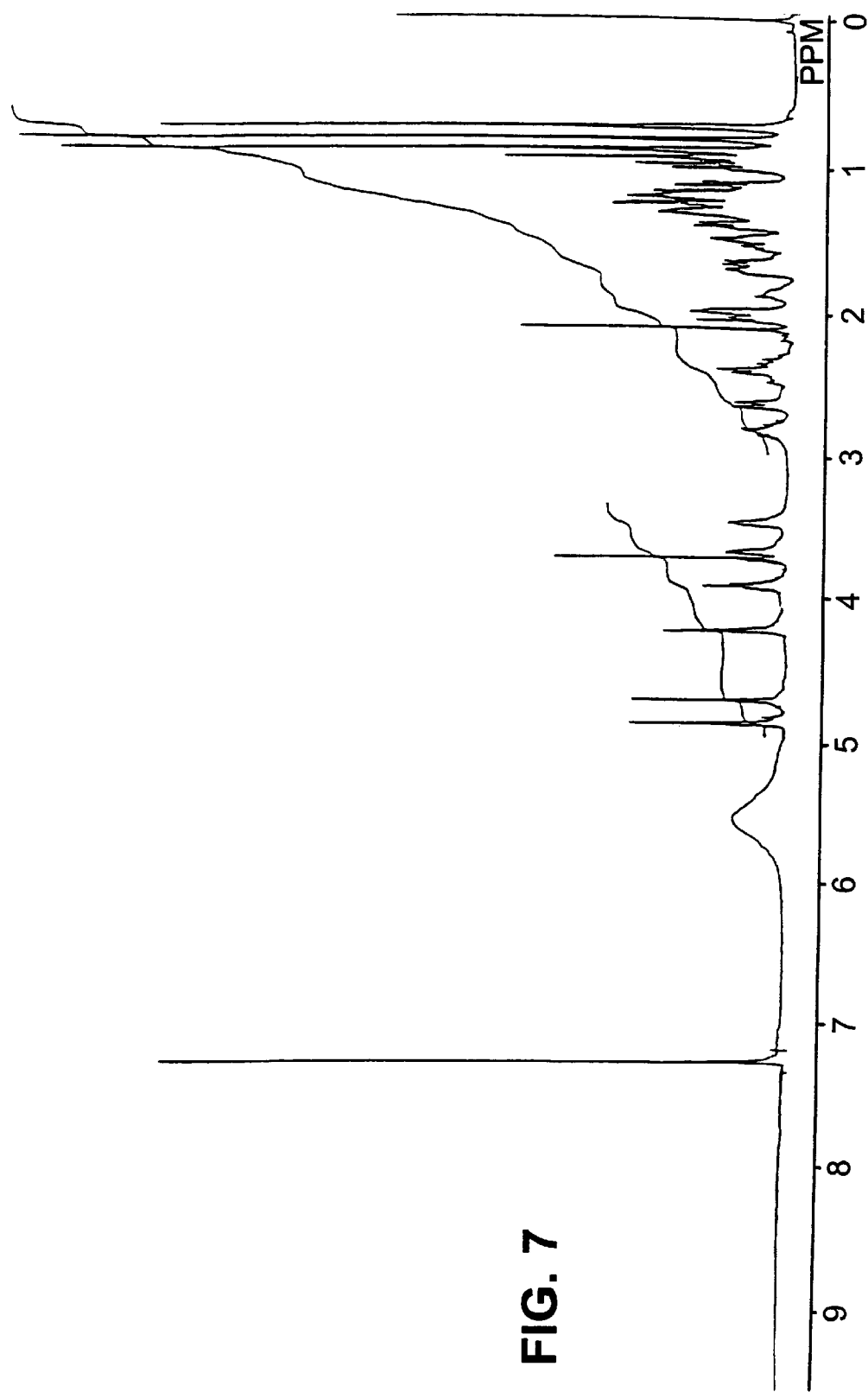
FIG. 7 shows a $^1$H-NMR chart of cryptoporic acid H.
Figure 8:
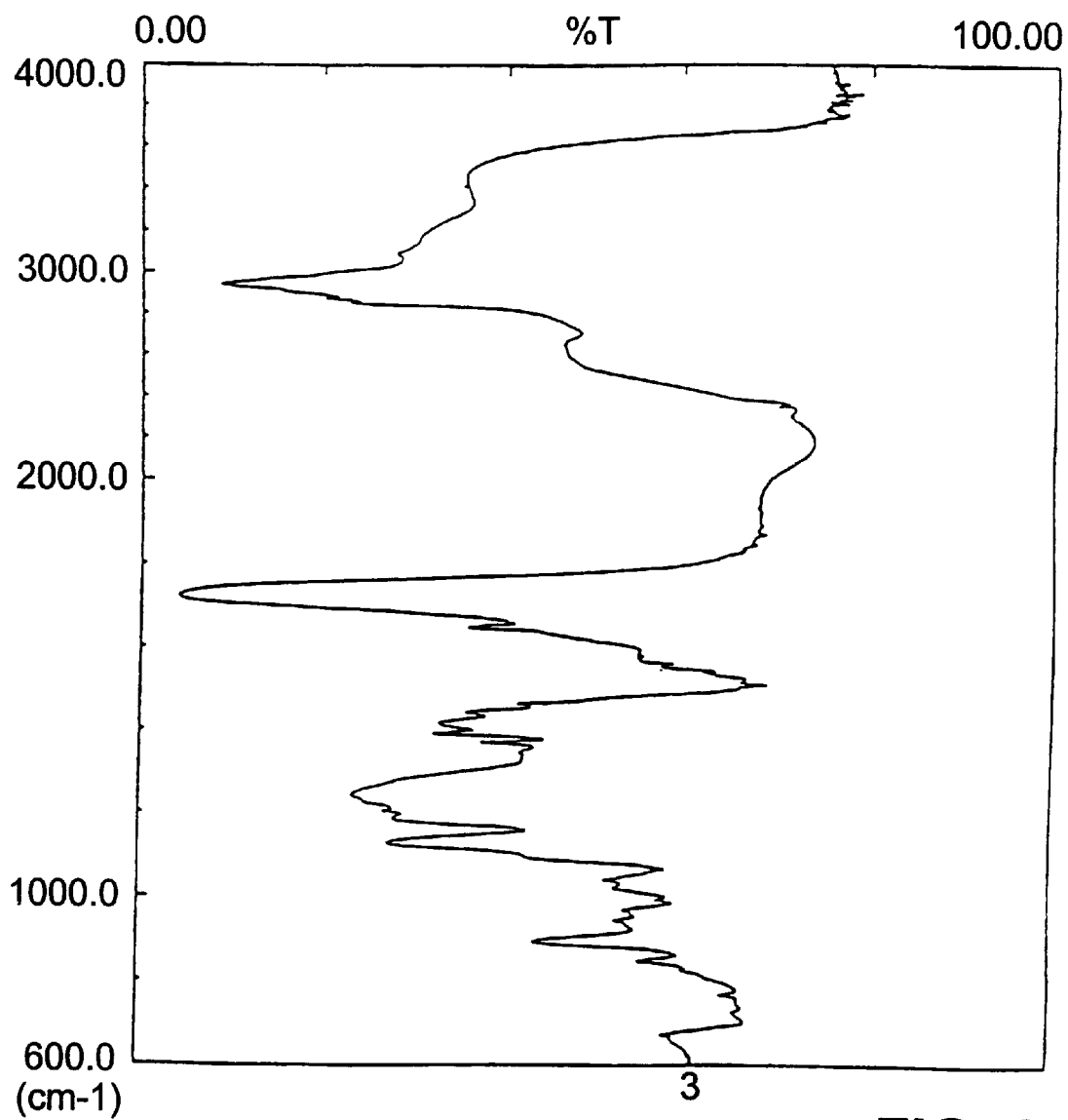
FIG. 8 shows the IR spectrum of cryptoporic acid H.

Cryptoporic acid H thus obtained was measured by $^1$H-NMR, $^{13}$C-NMR, and mass spectrometry. Data obtained were identical to those described in the literature (M. Hirotani et al., Phytochemistry 30(5): 1555–1559 (1991)), indicating that the compound was cryptoporic acid H. The $^1$H-NMR chart and IR spectrum of cryptoporic acid H are shown in FIGS. 7 and 8.

3 Cryptoporic acid H trimethyl ester represented by formula 10 was synthesized in the following manner.

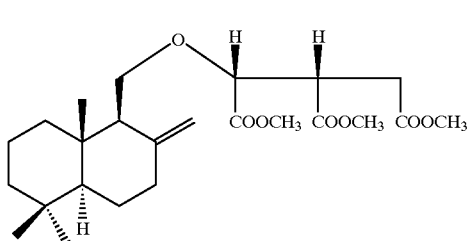

(10)

Like TG 103, a novel sesquiterpene compound (hereinafter referred to as TG 101, PCT/JP96/00315) was obtained by extracting fruiting bodies of *Roseofomes subflexibilis* (Berk. et Curt. z) Aoshi, a mushroom of the Polyporaceae family, with lower alcohol. This compound was hydrolyzed, and cryptoporic acid H thus obtained was methylated to obtain a trimethyl ester form.

Specifically, 1 ml of a 1 N sodium hydroxide aqueous solution was added to 1 ml of an ethanol solution of TG 101 (19 mg, 0.05 mmol) obtained in the same manner as described above, and the reaction solution was refluxed for 2 hours. After the reaction was completed, the reaction solution was diluted with water (3 ml) and washed twice with ethyl acetate (5 ml). The water phase was then made acidic with 1 N hydrochloric acid and extracted twice with ethyl acetate (5 ml). The extract was washed successively with water and saturated brine. After the ethyl acetate phase was dried over magnesium sulfate, the solvent was removed by distillation. The resulting residue was dissolved in methanol and treated with an ether solution of diazomethane. After the solvent was removed from the reaction solution by distillation, the resulting residuewas purified by silica gel column chromatography (eluant, n-hexane-ethyl acetate) to obtain 7 mg of cryptoporic acid H trimethyl ester as white powder.

Figure 9:
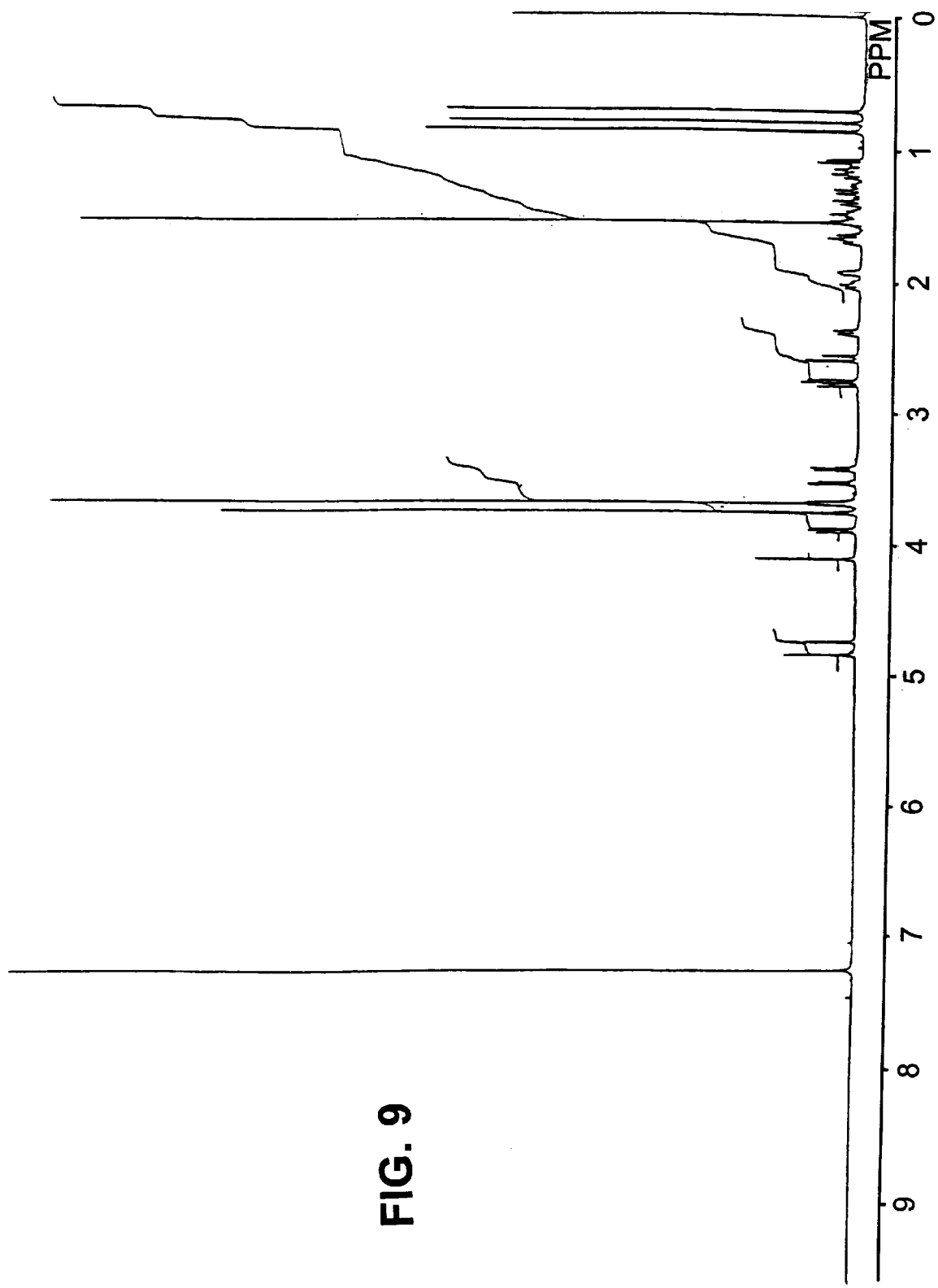
FIG. 9 shows a $^1$H-NMR chart of cryptoporic acid H trimethyl ester.
Figure 10:
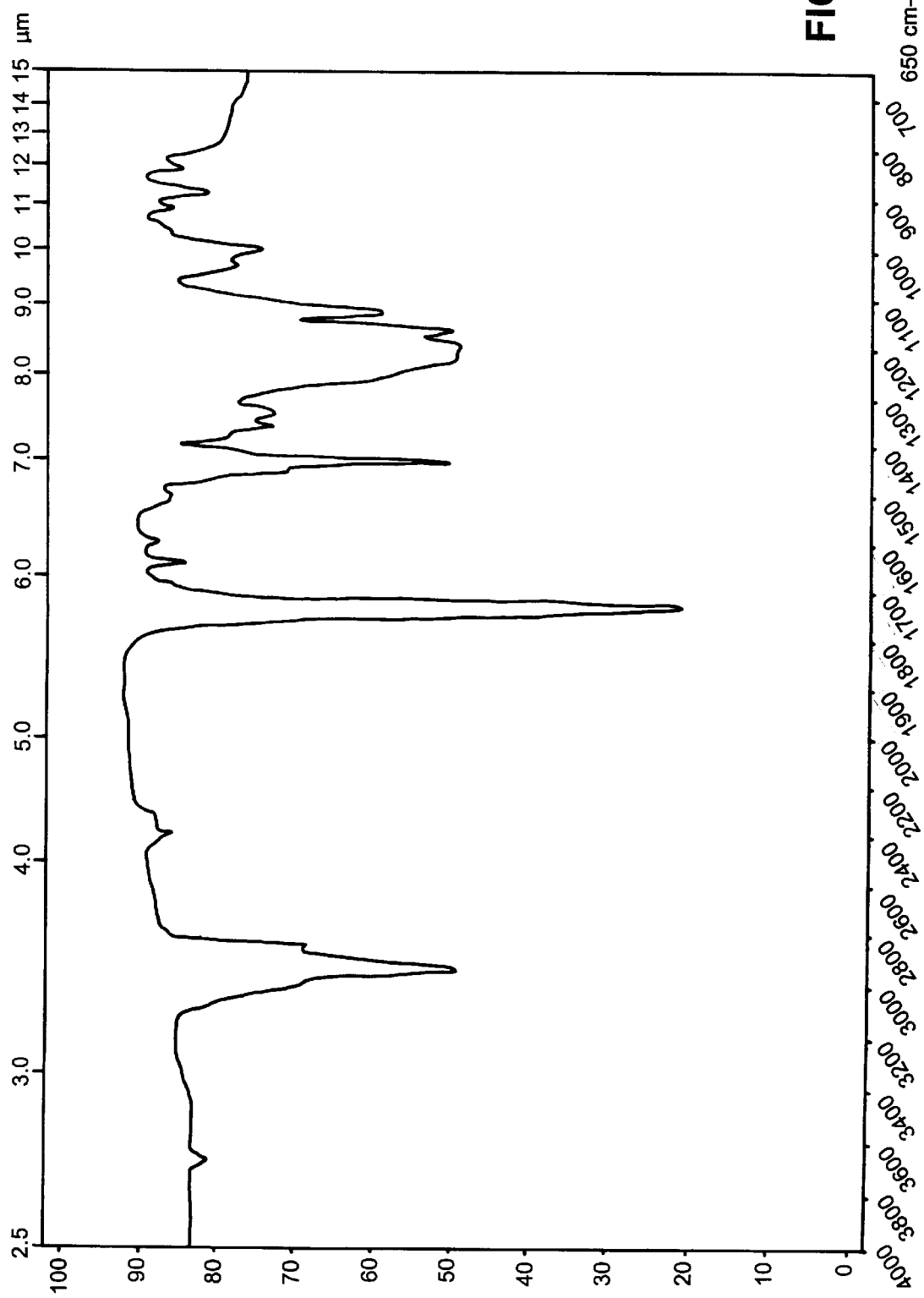
FIG. 10 shows the IR spectrum of cryptoporic acid H trimethyl ester.

Cryptoporic acid H trimethyl ester thus obtained was measured by $^1$HNMR, $^{13}$C-NMR, and mass spectrometry. Data were identical to those of cryptoporic acid A methyl ester described in the literature of Asakawa et al. (Trans. Mycol. Soc. Japan 29: 281–296 (1988) and Phytochemistry 31(2): 579–592 (1992)), indicating that the compound was cryptoporic acid H trimethyl ester. The $^1$H-NMR chart and IR spectrum of this compound are shown in FIGS. 9 and 10.

The structural formula (formula 11) and physicochemical properties of TG 101 are shown below.

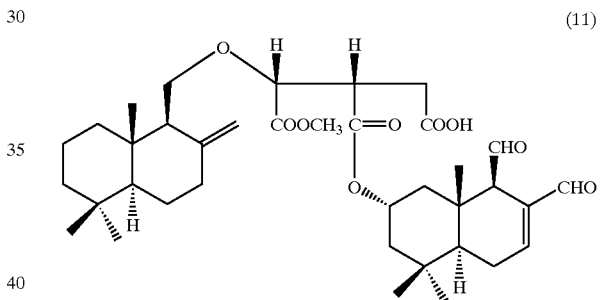

(11)

Figure 11:
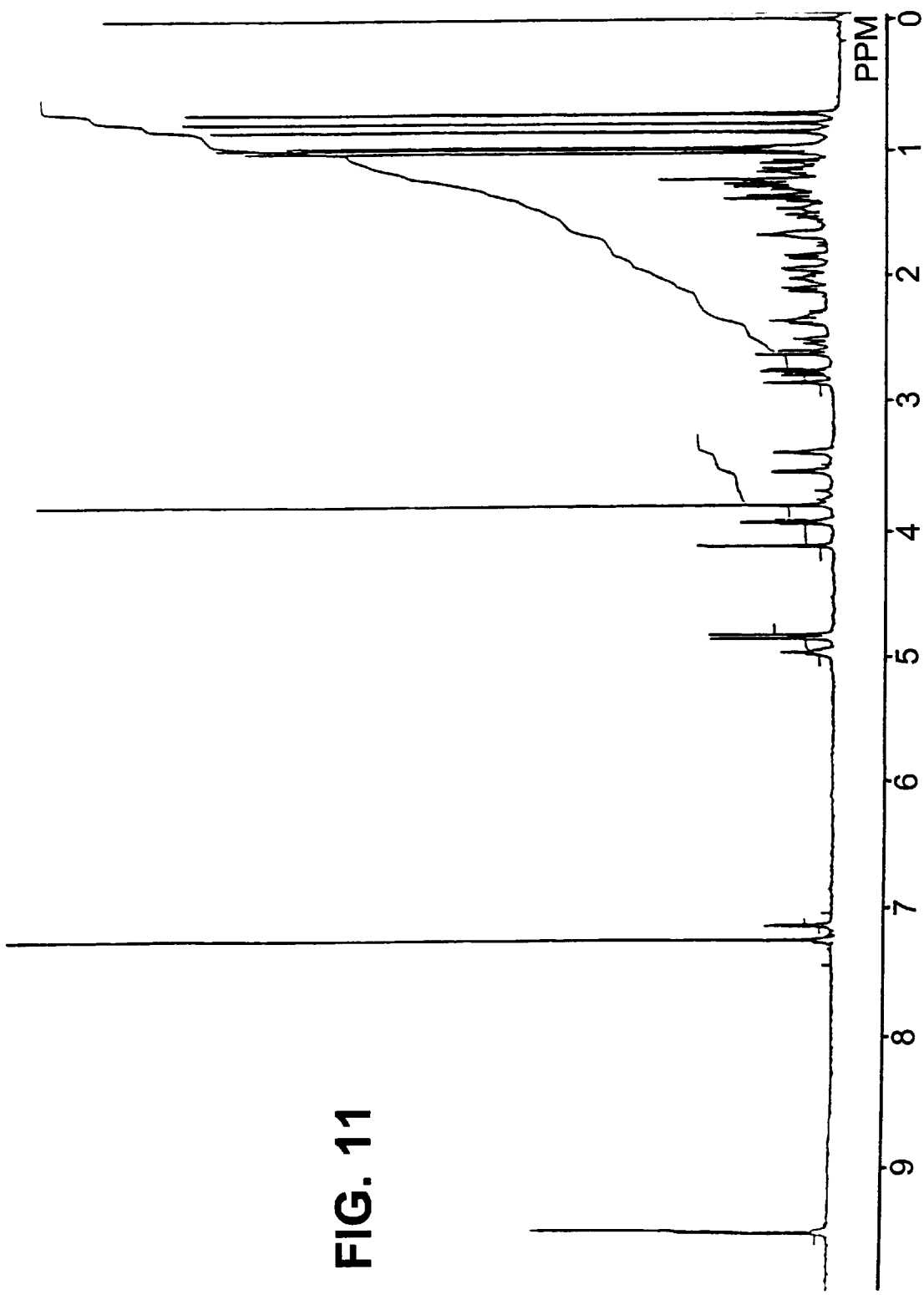
FIG. 11 shows the $^1$H-NMR spectrum of TG-103.
Figure 12:
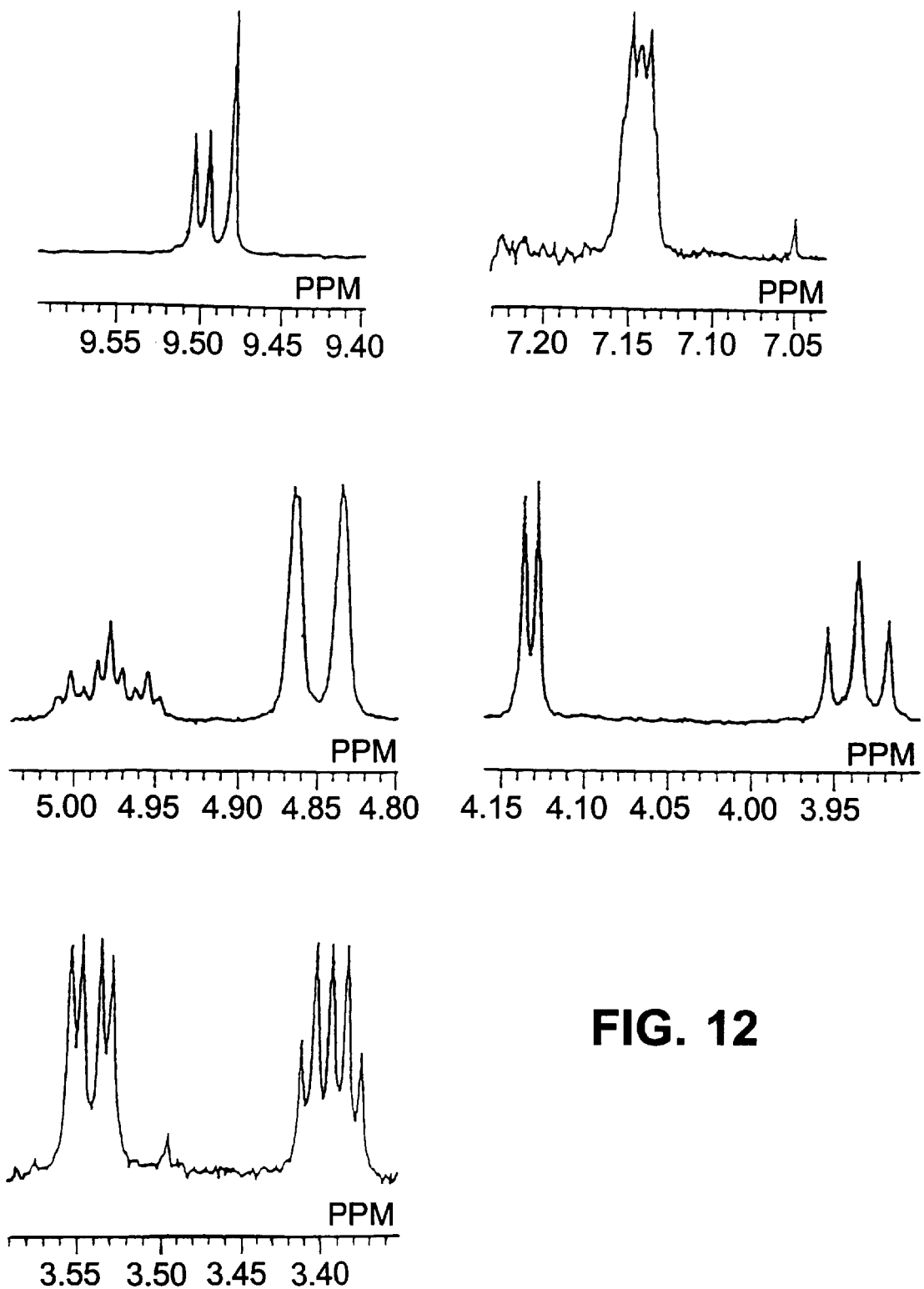
FIG. 12 shows a magnification of a part of the $^1$H-NMR spectrum of TG-103.
Figure 13:
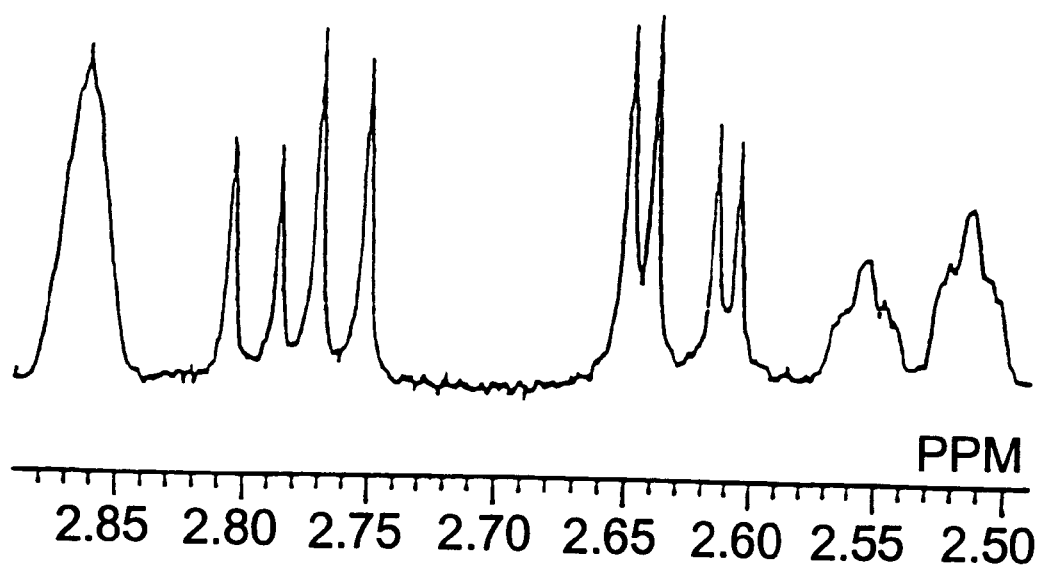
FIG. 13 shows a magnification of a part of the $^1$H-NMR spectrum of TG-103.
Figure 14:
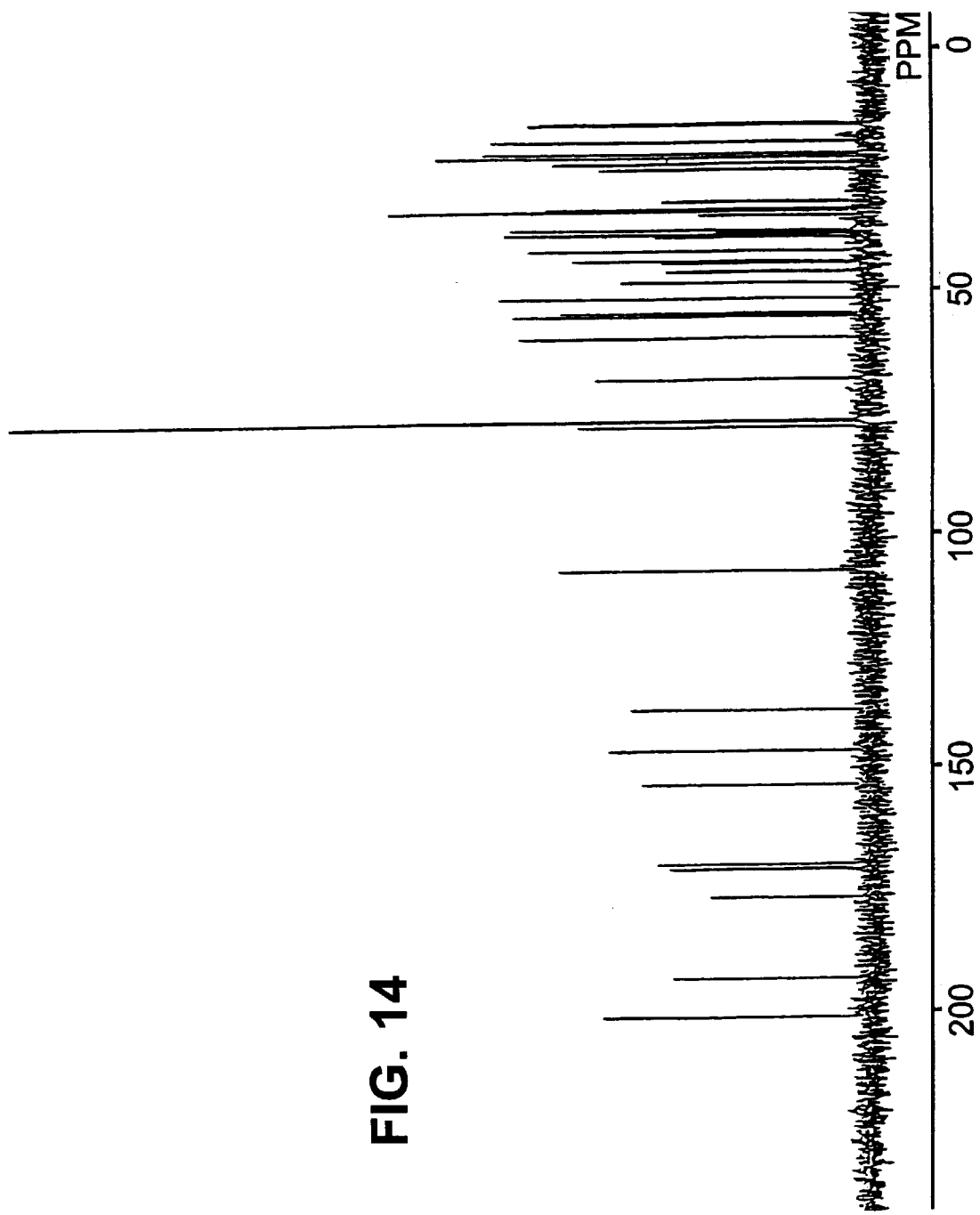
FIG. 14 shows the $^{13}$C-NMR spectrum of TG-103.

Physicochemical properties of TG 101
 (1) Appearance: Pale yellow, syrupy
 (2) Specific rotation: $[\alpha]_D^{24}$ –20.9° (c=0.23, chloroform)
 (3) Molecular weight: 642
 (4) Molecular formula: $C_{37}H_{54}O_9$
 (5) EI mass spectrum: m/z 642 (M$^+$)
 (6) HREI mass spectrum: m/z 642.3748 (M$^+$:$C_{37}H_{54}O_9$) Found: 642.3768
 (7) Ultraviolet absorption spectrum(nm)$\lambda_{max}$ (MeOH) (logε): 201 (4.12), 228 (3.98), 296 (2.96)
 (8) Infrared absorption spectrum (cm$^{-1}$) υmax (CHCl$_3$): 3600–2400 (br), 2925, 2850, 1750 (sh), 1720, 1680, 1640, 1460, 1440, 1380, 1360, 1300–1200 (br), 1170, 1130
 (9) $^1$H-NMR spectrum: As shown in FIGS. 11 to 13
 (10) $^{13}$C-NMR spectrum: As shown in FIG. 14
 (11) Solubility:
  Easily soluble in methanol, acetone, and ethyl acetate; soluble in chloroform; and slightly soluble in water
 (12) Rf value: Silica gel thin-layer chromatography with Kieselgel
  60 F$_{254}$ (Merck)

0.46 (chloroform/methanol=90/10)

0.17 (chloroform/ethyl acetate/methanol=15/5/1)

(13) Color reaction: Ehrlich reagent-positive (purple red)

4. Fruiting bodies of *Roseo subflexibilis* (5.9 kg) collected in Makabe-cho in Ibaraki prefecture in June 1995 were crushed to approximately 2 to 3 cm cubes and dried at room temperature. Dried fruiting bodies (2.9 kg) were soaked in methanol (15 L) and extracted at room temperature for one day. After the resulting extract was concentrated to about 200 ml under reduced pressure, the concentrate was extracted three times with an equal volume of ethyl acetate. This extraction procedure was repeated twice. Each of the ethyl acetate extracts was confirmed to contain the desired compound by thin-layer chromatography, and the extracts were combined.

The ethyl acetate extract (64 g) was then divided into four portions, each of which was about 15 g. Each portion was subjected to silica gel column chromatography (150 g, 5 cm ID×17 cm). Elution was conducted using a chloroform/ethyl acetate mixed solvent (90/10, 80/20) and a chloroform/methanol mixed solvent (95/5, 90/10, 80/20, 25/75). Fractions eluted with each solvent were combined. The fraction (5.5 g) eluted with chloroform/methanol=95/5 was subjected to silica gel column chromatography (92 g, 4 cm ID×14 cm; eluent, chloroform/methanol=100/1 to 100/25) to obtain the fraction eluted with 100/2 (2.0 g). Likewise, the fraction (16.0 g) eluted with chloroform/methanol=90/10 was subjected to silica gel column chromatography to obtain the fraction eluted with 100/2 (3.2 g). These fractions were combined and fractionated by conducting similar silica gel column chromatography several times in the same manner to obtain 328 mg of the fraction eluted with chloroform/methanol=100/2. This fraction was fractionated by column chromatography using 10% hydrated silica gel (40 g, 3.0 cm ID×9 cm; eluent, hexane/ethyl acetate=2/1, 1/1, 1/2, 1/3, 1/4) to obtain 221 mg of the fraction eluted with hexane/ethyl acetate=1/1. The resulting fraction was further fractionated by reverse phase column chromatography (1.7 cm ID×9 cm; eluent, 70 to 100% methanol) to obtain 100 mg of the 80 to 85% ethanol-eluted fraction. This fraction was fractionated by column chromatography using 10% hydrated silica gel (10 g, 1.5 cm ID×9.5 cm; eluent, chloroform/methanol=100/0.25 to 100/10) and 77 mg of the fraction eluted with chloroform/methanol=100/0.5 to 100/1. This fraction was recrystallized from hexane/ethyl acetate to obtain 40 mg of a cryptoporic acid derivative represented by formula 3 as colorless, columnar crystals.

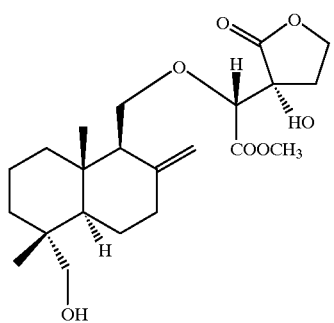

(3)

Physicochemical properties of the resulting compound are as follows.

(1) Appearance: Colorless, columnar crystals (2) Molecular weight: 394

Figure 15:
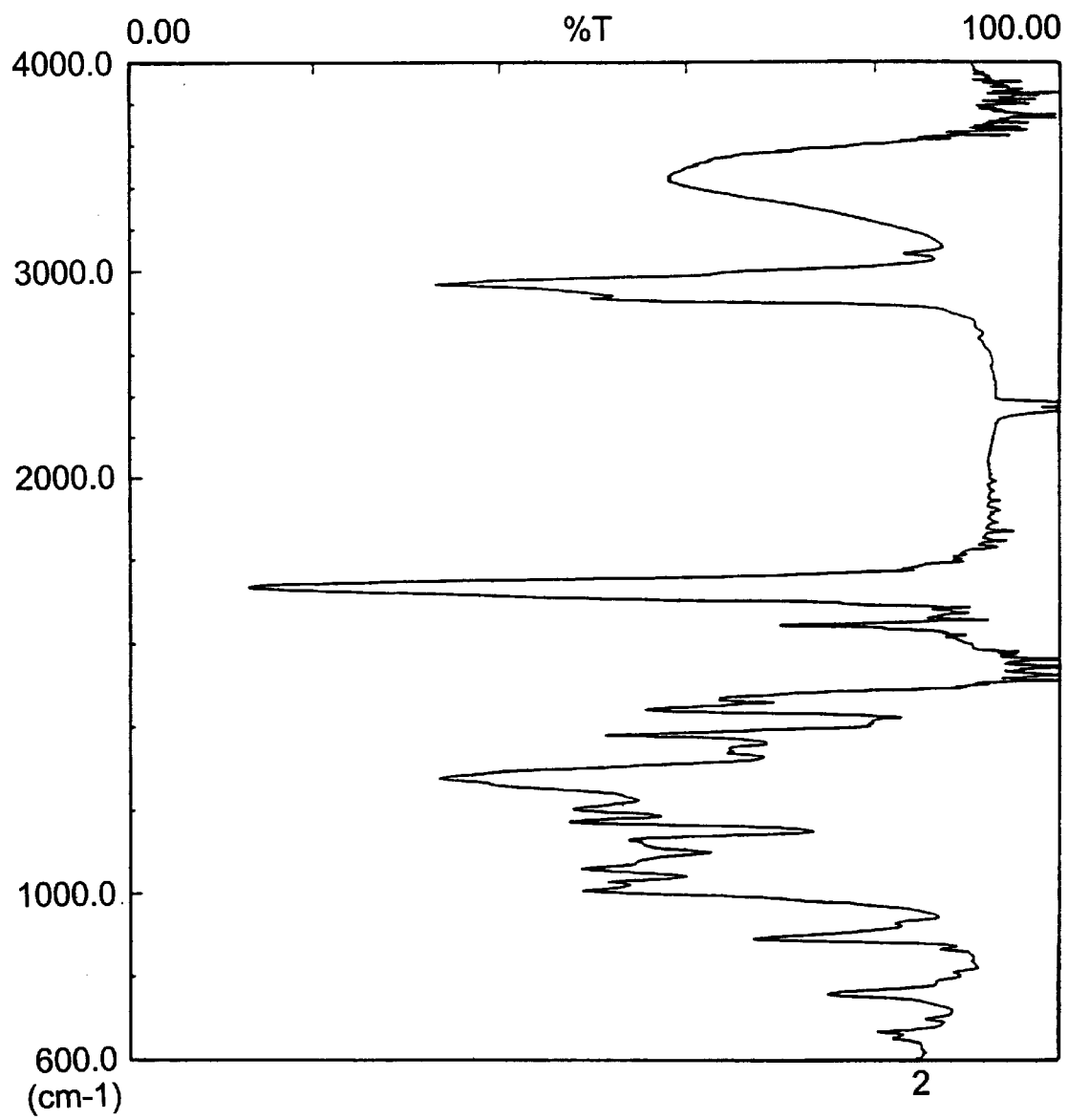
FIG. 15 shows the infrared absorption spectrum of the compound of formula 3.

(3) Molecular formula: $C_{22}H_{34}O_6$ (4) Infrared absorption spectrum (KBr): As shown in FIG. 15

Figure 16:
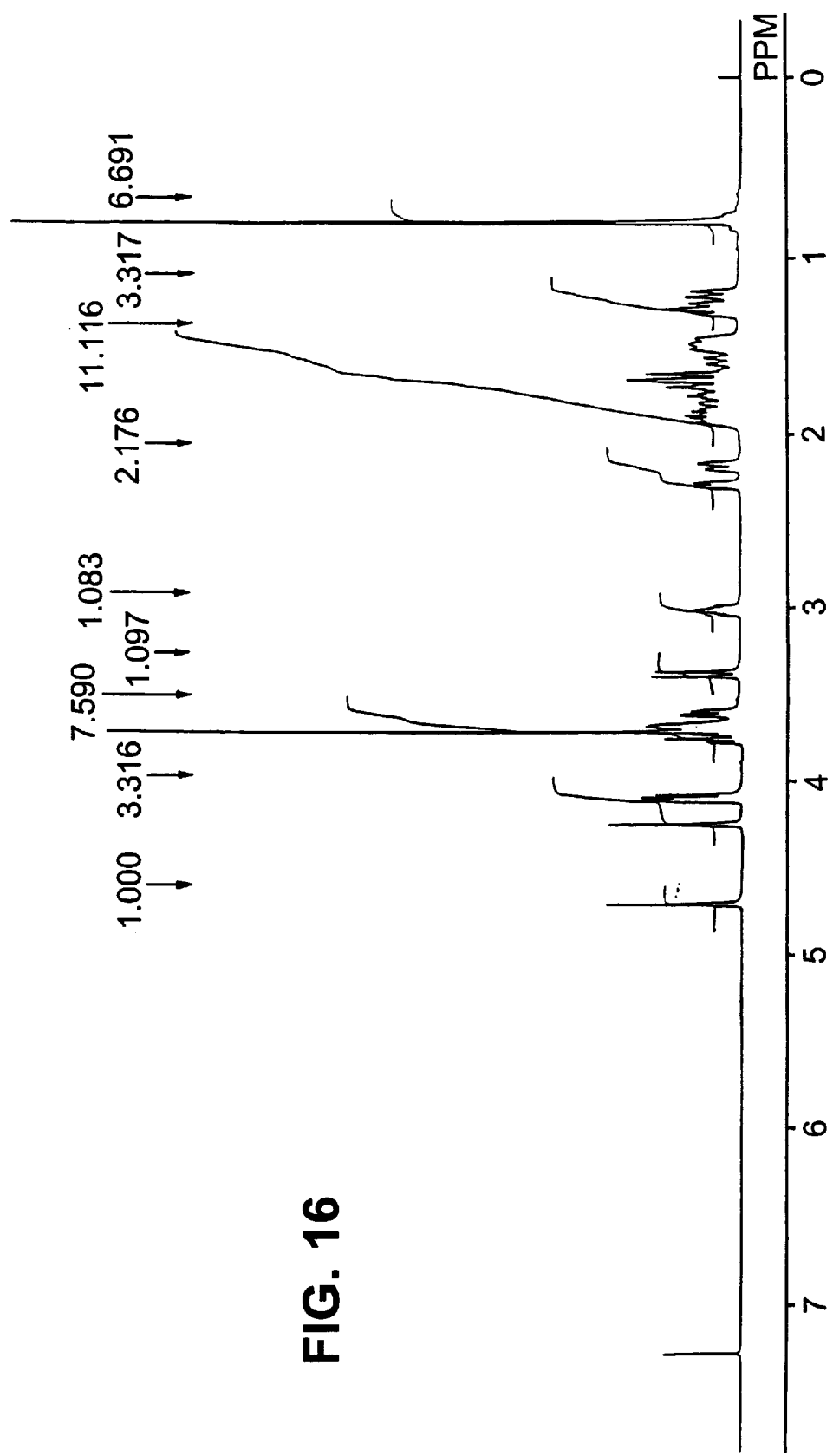
FIG. 16 shows the 500 MHz $^1$H-NMR spectrum (CDCl$_3$) of the compound of formula 3.

(5) 500 MHz $^1$H-NMR spectrum ($CDCl_3$): As shown in FIG. 16

Figure 17:
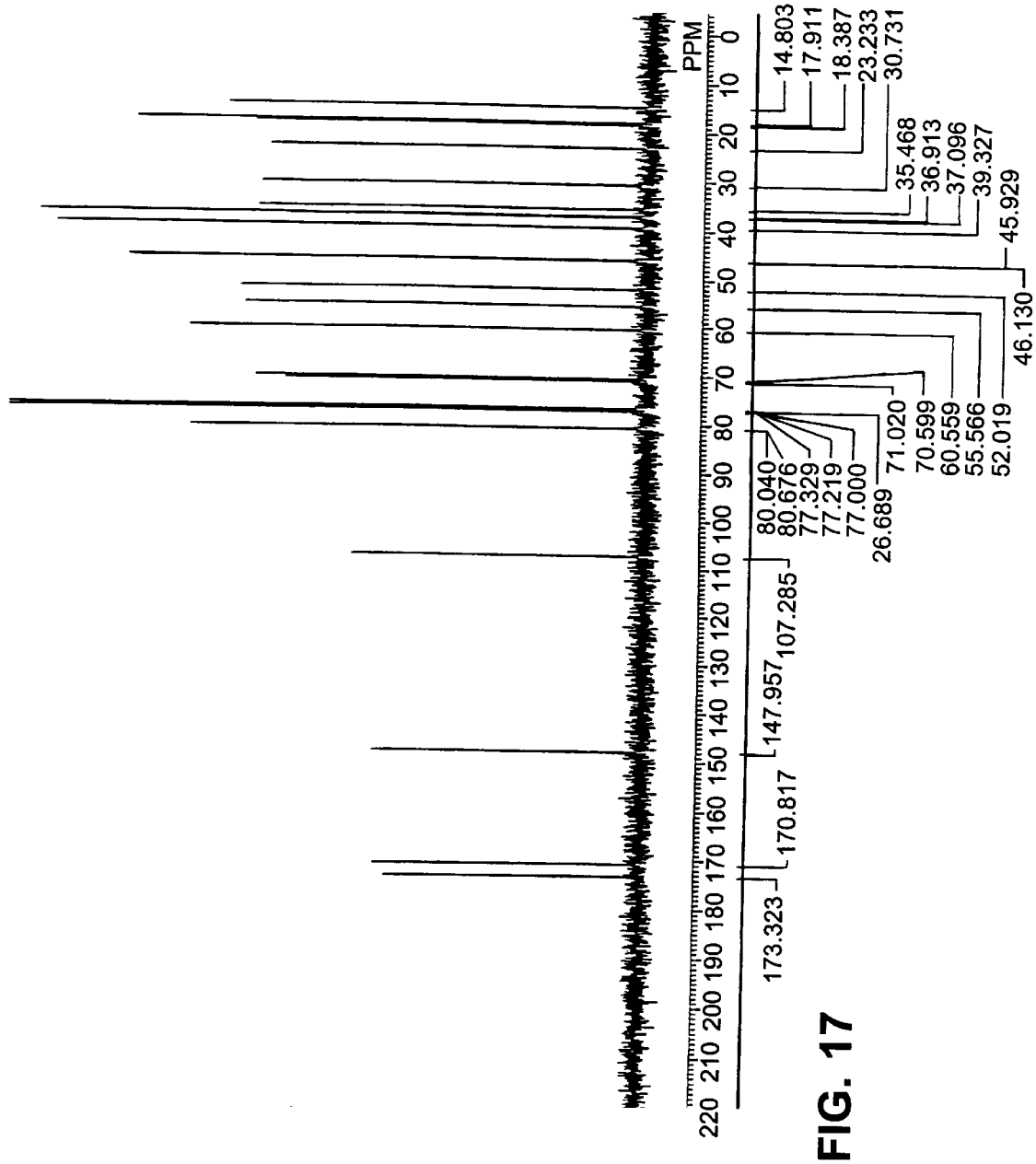
FIG. 17 shows the 125 MHz $^{13}$C-NMR spectrum (CDCl$_3$) of the compound of formula 3.

(6) 125 MHz $^{13}$C-NMR spectrum ($CDCl_3$): As shown in FIG. 17

(7) Rf value:

Silica gel thin-layer chromatography, 0.58 [Kieselgel 60 $F_{254}$ (Merck); developing solvent, chloroform-methanol=10/1]

Reverse phase silica gel thin-layer chromatography, 0.30 [RP18 F254 S (Merck); developing solvent, 90% methanol.

(8) Color reaction: Ehrlich reagent-positive (purple red)

Anisaldehyde reagent-positive (bluish purple)

50% sulfuric acid reagent-positive (brown)

TEST EXAMPLE 1

Measurement of Antifungal Activity

1. Antifungal activities of cryptoporic acids A, B, and D obtained as described above were determined.

Using *Candida albicans, Aspergillus niger, Aspergillus fumigatus,* and *Cryptococcus neoformans* as test fungi, in vitro antifungal activities were determined to confirm the antifungal activities of cryptoporic acids A, B, and D. The test method and the results are shown below.

The fungal strains used for this test were standard strains provided by Teikyo University, Institute of Medical Mycology. Drug sensitivity was measured using Yeast Morphology Agar (Difco) as media.

The test fungi were spread over slant made of a potato dextrose agar medium (NissuiSeiyaku) and cultured at 30° C. for one day (Candida, Cryptococcus) or four days (*Aspergillus niger, Aspergillus neoformans*). After culturing, fungi on the slant were washed away with sterile physiological saline supplemented with 0.1% Tween 80. The solution was passed through a filter with 15 $\mu$m pores. The fungi were counted on a hemocytometer and adjusted to $10^5$ CFU/ml to serve as an inoculation solution. A 0.02 ml portion of this solution was inoculated into Yeast Morphology Agar containing test agents by two-fold serial dilution and cultured at 30° C. for 1 or 4 days.

Antifungal effect was judged with naked eyes. Concentrations at which evident inhibition of growth was observed compared with control media containing no drug were taken as MIC values.

Antifungal activities of cryptoporic acid derivatives determined in the above test are shown in Tables 1 and 2.

TABLE 1

| | MIC (*Candida albicans*) |
|---|---|
| Cryptoporic acid A | 25 $\mu$g/ml |
| Cryptoporic acid B | 25 $\mu$g/ml |
| Cryptoporic acid D | 100 $\mu$g/ml |

TABLE 2

| | MIC (*Aspergillus fumigatus*) |
|---|---|
| Cryptoporic acid B | 200 $\mu$g/ml |

2. Antifungal activity of cryptoporic acid H was measured as follows.

*Candida albicans, Aspergillus niger, Aspergillus fumigatus,* and *Cryptococcus neoformans* were used as test fungi. The test for in vitro antifungal activity was conducted in the same manner as in 1 above to confirm antifungal activity. Results are shown in Table 3.

TABLE 3

|  | MIC |
|---|---|
| *Candida albicans* TIMM1623 | 200 μg/ml |
| *Aspergillus niger* TIMM0113 | 200 μg/ml |
| *Aspergillus fumigatus* TIMM0063 | 200 μg/ml |
| *Saccharomyces cerevisiae* JCM2216 | 200 μg/ml |

3. In vitro antifungal activities of cryptoporic acid derivatives represented by formula 3 and a commercially available antifungal agent, Diflucan, were tested using *Candida albicans* as test fungi in the same manner. Results are shown in Table 4.

TABLE 4

| | MIC μg/ml | |
|---|---|---|
| fungal strain\drugs | cryptoporic acid derivatives | Diflucan |
| *C. albicans* TIMM1623 | 25 | 25 |

EXAMPLE 2

Infection-Treating Test

*Candida albicans* ($1.0 \times 10^6$ CFU/mouse) or *Aspergillus fumigatus* ($2.0 \times 10^6$ CFU/mouse) was suspended in physiological saline, and a 0.2 ml portion of each solution was injected into healthy grown mice (ICR, 4 week-old, female, 19–22 g, Nihon CLEA) via the caudal vein to establish infection.

Cryptoporic acid H was dissolved in sesame oil in prescribed concentrations, and a 0.2 ml portion was orally administered per dose to the mice through a stomach probe. The first administration was conducted 1 hour after inoculation of fungi. Thereafter, administration was conducted six times (once a day every 24 hours; for a total of seven days). only the base (0.2 ml) was administered to the control group.

Treatment effectiveness was evaluated with $ED_{50}$ by using the Weil method from the survival rate of treated mice when all the control animals died. The results were as shown in Table 5.

TABLE 5

| Fungal strain | $ED_{50}$ |
|---|---|
| *Candida albicans* | 0.32 mg/kg |
| *Aspergillus fumigatus* | 2.0 mg/kg |

Industrial Applicability

Antitifungal agents comprising a cryptoporic acid derivative of the present invention or a dimer thereof as an active ingredient are expected to be both effective antifungal agents themselves and useful as startingmaterials for producing compounds with antifungal activity. The derivatives possess antifungal activities against fungi such as *Candida albicans, Aspergillus niger, Aspergillus fumigatus,* and *Cryptococcus neoformans* superior to those of commercially available antifungal agents and can produce excellent effects as antifungal agents.

What is claimed is:

1. A method for treating mycosis which comprises administering to an animal in need thereof an effective amount of a cryptoporic acid derivative with a hydroxyl group represented by formula 1 or a dimer thereof:

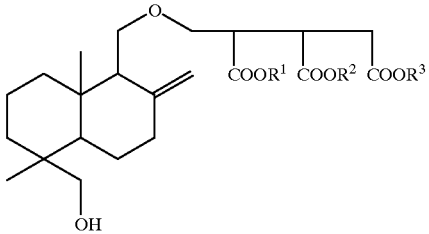

(1)

wherein $R^1$, $R^2$, and $R^3$ are the same or different and each is hydrogen, an alkyl group, or an alkali metal, or —$COOR^2$ and —$COOR^3$ optionally form a lactone ring.

2. The method of claim 1, wherein $R^1$, $R^2$, and $R^3$ are the same or different and each is hydrogen or a lower alkyl group.

3. The method of claim 1, wherein each of $R^1$ and $R^2$ is a methyl group, and $R^3$ is hydrogen.

* * * * *